United States Patent [19]
Varano et al.

[11] 4,038,055
[45] July 26, 1977

[54] GAS CHROMATOGRAPH FOR CONTINUOUS OPERATION WITH INFRARED SPECTROMETER

[75] Inventors: Antonio Varano, Philadelphia, Pa.; Reginald Tobias, Watertown, Mass.

[73] Assignee: Block Engineering, Inc., Cambridge, Mass.

[21] Appl. No.: 621,404

[22] Filed: Oct. 10, 1975

[51] Int. Cl.² ............................................. B01D 15/08
[52] U.S. Cl. ........................................ 55/197; 55/386; 55/267; 23/232 C
[58] Field of Search ................... 55/67, 197, 386, 267; 23/232 C; 73/23.1

[56] References Cited
U.S. PATENT DOCUMENTS

| | | | |
|---|---|---|---|
| 3,581,465 | 6/1971 | Haruai et al. | 55/67 |
| 3,841,059 | 10/1974 | McCabe | 55/386 X |
| 3,880,587 | 4/1975 | Szakasits et al. | 23/232 C |
| 3,897,679 | 8/1975 | Guild | 73/23.1 |

Primary Examiner—John Adee
Attorney, Agent, or Firm—Robert L. Slater, Jr.

[57] ABSTRACT

An improved gas chromatograph for "on line" use with absorption spectrum analyzers, particularly, infrared spectrometers. The new chromatograph has been adapted for compatibility with a variety of absorption spectrum analysis instruments from the standpoint of cycling time, dimensions, thermal characteristics and convenience in handling extremely small and highly reactive chemical sample materials.

8 Claims, 3 Drawing Figures

GAS CHROMATOGRAPH FOR CONTINUOUS OPERATION WITH INFRARED SPECTROMETER

CROSS REFERENCES TO RELATED APPLICATIONS

Certain portions of the apparatus and method of the present invention are not our invention but are the inventions of TOMAS HIRSCHFELD and DAVID BROWN, as defined in the claims of their applications, Ser. No. 553,989, filed Feb. 28, 1975, and TOMAS HIRSCHFELD and HAROLD MC NAIR, as defined in the claims of their application, Ser. No. 553,990, filed Feb. 28, 1975. The above referenced applications are assigned to the assignee of the present invention.

BACKGROUND OF THE INVENTION

1. Field of the Invention

The present invention relates to gas chromatograph devices, and specifically pertains to a compact improved gas chromatograph device for "on line" use in combination with absorption spectrum analyzers, particularly, infrared spectrometers 2. Description of the Prior Art Chromatograph elution of a mixture of sample vapors is a common laboratory procedure. The separated sample components issue from the chromatograph column at a rate determined by many factors, among which is the carrier gas flow velocity. The efficiency of the chromatographic separation is dependent upon operation of the column at, or very near, the optimum carrier gas velocity for the given column conditions. The most efficient chromatographs emit well spaced eluted sample mixture components characterized by narrow peak widths as shown on chromatograph charts. That is, eluted samples are preferably issued from the chromatograph column in the briefest time interval measured from leading edge to trailing edge of peak.

On the other hand, absorption spectrum analyzers require a fixed, and in a given spectrometer, an irreducible period of time to scan the sample through the selected frequency range, process and record the resultant data. The infrared spectrometer is, at present, the most widely used laboratory chemical identification absorption spectrum analyzer.

The time of response of presently available infrared spectrometers is approximately an order of magnitude longer than the presently available efficient gas chromatograph output peak transit time. As a consequence, these two instruments are not normally compatible when directly connected one to another, but may be used in combination for the separation and identification of chemical compounds only by skillful and time consuming manipulations performed by qualified technicians. Previous practice has comprised catching and storing in separate sample cells the eluted sample peaks issuing from a chromatograph column, then placing the separate sample cells, one by one, in the spectrometer for the required time to complete the spectrometer analysis. "On line" operation of a gas chromatograph in combination with an absorption spectrum analyzer, such as an infrared spectrometer, has for full spectrum range analysis, not been feasible to this date.

Because of the cumbersome procedures for wide frequency band absorption spectrum analysis of eluted samples, a practice referred to as analysis, "on the fly" has been developed. The eluted sample peak is passed through the spectrometer "on the fly" and absorption spectra data is recorded, as may be obtained in the brief interval of time the sample material requires to pass the windows of a flow through sample cell. An experienced analytical chemist can utilize the fragmentary absorption spectrum "fly" data to provide useful sample compound identification clues. The "fly" spectrometer analysis is a compromise and a limited value substitute for the full frequency spectrum scan analysis.

Additional problems attend present practices for combining gas chromatographic devices with absorption spectrum spectrometers, particularly, infrared spectrometers. Sample compounds issue from chromatograph columns at elevated temperatures. Present chromatographs require bulky ovens and temperature control paraphernalia. The higher temperatures of the chromatograph, if mounted adjacent to an infrared spectrometer without special heat shielding, would interfere with the operation of the spectrometer.

It is common practice to operate gas chromatograph columns at programmed elevated temperatures selected to assure proper volatility of all elutant sample components. Abrupt temperature changes of elutants, as these issue from a chromatograph column and are caught and stored temporarily in sample cell containers awaiting spectrometer analysis, may give rise to altered physical states of the eluted samples. Rapid cooling of eluted samples may result in condensation on the sample cell windows. All of the foregoing effects adversely degrade the absorption spectrum analysis data.

Reduction in the number of required hand manipulations of toxic and dangerous materials during analysis and production quality control procedures is an important safety advantage. No presently available gas chromatograph provides compatible means for matching the chromatograph output directly with an infrared spectrometer. As a consequence, dangerous toxic elutants must be hand transferred fro the chromatograph output to a spectrometer sample cell. After the spectrum analysis is completed, the toxic sample contents of the sample cell must be cleared. All these presently required steps involve separate hand manipulations and incur some element of hazard. Continuous "on stream" management of dangerous materials significantly reduces the risks of loss or dispersion of toxic sample materials.

The incompatibility of presently available gas chromatographs and infrared spectrometers is not only limited to time incompatibility. The shear size and vertical dimensions of present chromatographs, as compared with spectrometer sample cell dimensions, makes the direct physical matching of chromatograph output to spectrometer sample cell apparatus awkward. The different ambient temperature requirements for operation of the two kinds of instruments, as referred to above, further complicates "on line" matching of presently available chromatographs and infrared spectrometers.

The chromatograph column emits large volumes of gaseous effluent, some of which may be combined with portions of reactive corrosive sample mixture vapors. Infrared spectrometers are sensitive complex instruments easily damaged by corrosive chemicals. Direct physical combination of the output of gas chromatograph devices with infrared and other absorption spectrum spectrometers in the absence of special precaution, risks corrosion and damage to sensitive spectrometer working parts.

There is, accordingly, a need for a gas chromatograph device that may be conveniently and compatibly combined directly with absorption spectrum analyzer equipment. Particularly, there is a present need for a compact easily operated gas chromatograph suitable for "on line" combination with infrared spectrometers.

OBJECTS AND ADVANTAGES OF THE PRESENT INVENTION

A first object of the present invention is to provide a compatible general purpose gas chromatograph for "on line" combination operation with absorption spectrum spectrometers.

Another object of the present invention is to provide an easily operated gas chromatograph having dimensions, thermal properties and operating time characteristics compatible with juxtaposed mounting to and simultaneous "on line" operation with, presently available laboratory infrared spectrometers.

Still another object of the present invention is to provide a compact compatible gas chromatograph wherein the column output is connected directly to a sample cell means within an absorption spectrum spectrometer.

Yet another object of the present invention is to provide a compact, safe gas chromatograph having means for compatibly matching the chromatograph operation time to the response time of presently available infrared spectrometers.

These and other objects and advantages of my invention will be evident from the drawings, specification and claims below.

SUMMARY OF THE INVENTION

An improved novel gas chromatograph for combination with absorption spectrum analyzers, particularly, infrared spectrometers. The chromatograph adapted to be compactly mounted; the various chromatograph components are separately thermostated and thermally insulated from one another and from excessive transfer of heat to adjacent equipment. A valved flow through sample cell is positioned transversely within the chromatograph and adapted to provide "on line" test sample material for "on line" absorption spectrum analysis. Means for adjusting the chromatograph time response to a rate compatible with absorption spectrum analysis procedure rates, particularly for infrared spectrometer frequency scan cycle rate is provided in the invention.

DESCRIPTION OF THE INVENTION

Figure 1:
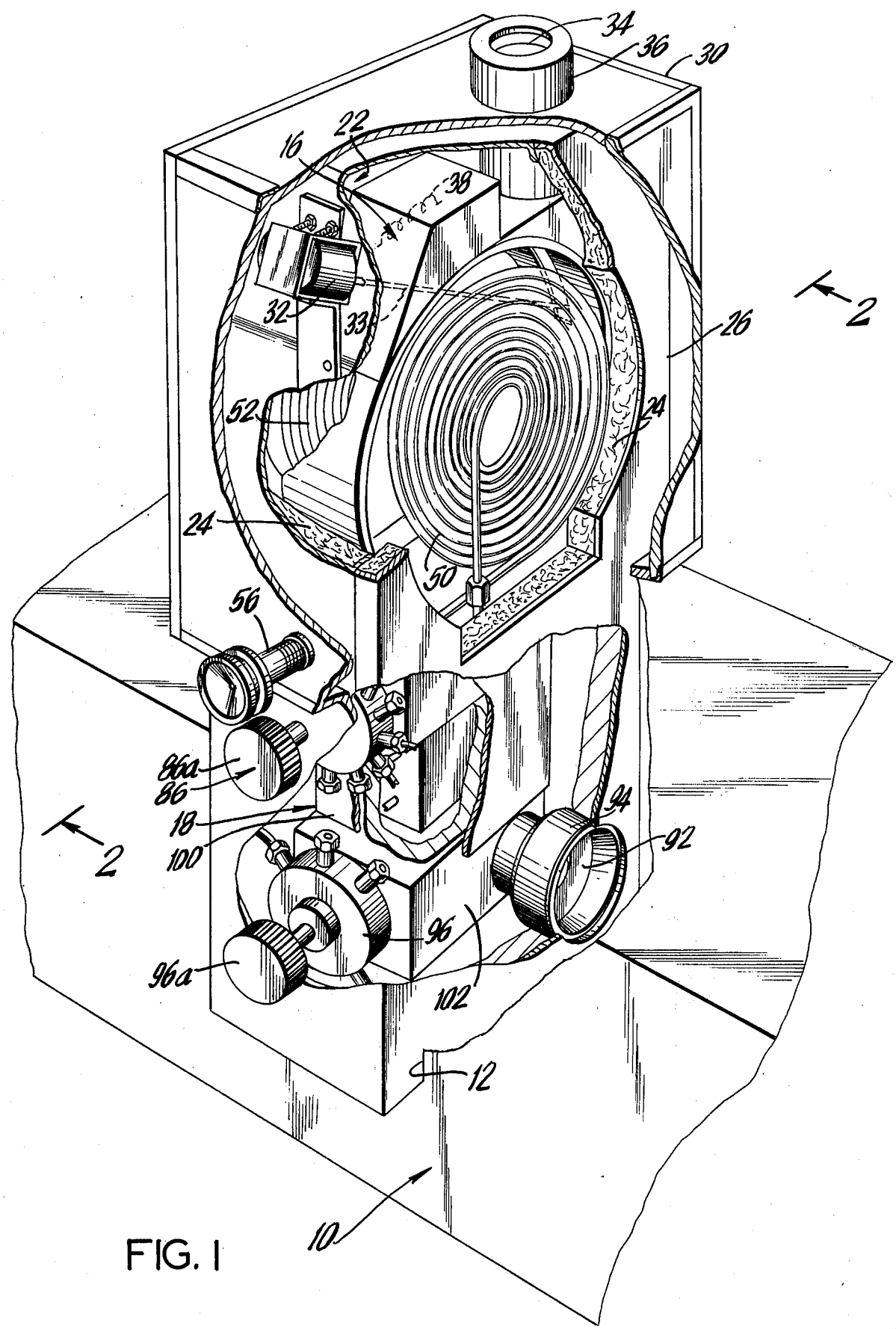
FIG. 1 is a perspective view, partially cutaway, of a preferred embodiment of my invention.

A partially cutaway perspective view of a preferred embodiment of our invention is shown in FIG. 1, wherein an absorption spectrum analyzer 10 is shown in fragmentary form. For purposes of the present description, the absorption spectrum analyzer used is an infrared spectrometer. However, our combination of chromatograph and absorption spectrum analyzer is intended to encompass within the combination any spectrum analyzer chosen from the variety of ultra-violet visible band, raman and other available absorption spectrum analyzer instruments. The infrared spectrometer 10, shown in the illustrations, is provided with a test sample well 12, into which a test sample cell is normally inserted for performing the analysis procedure.

Figure 2:
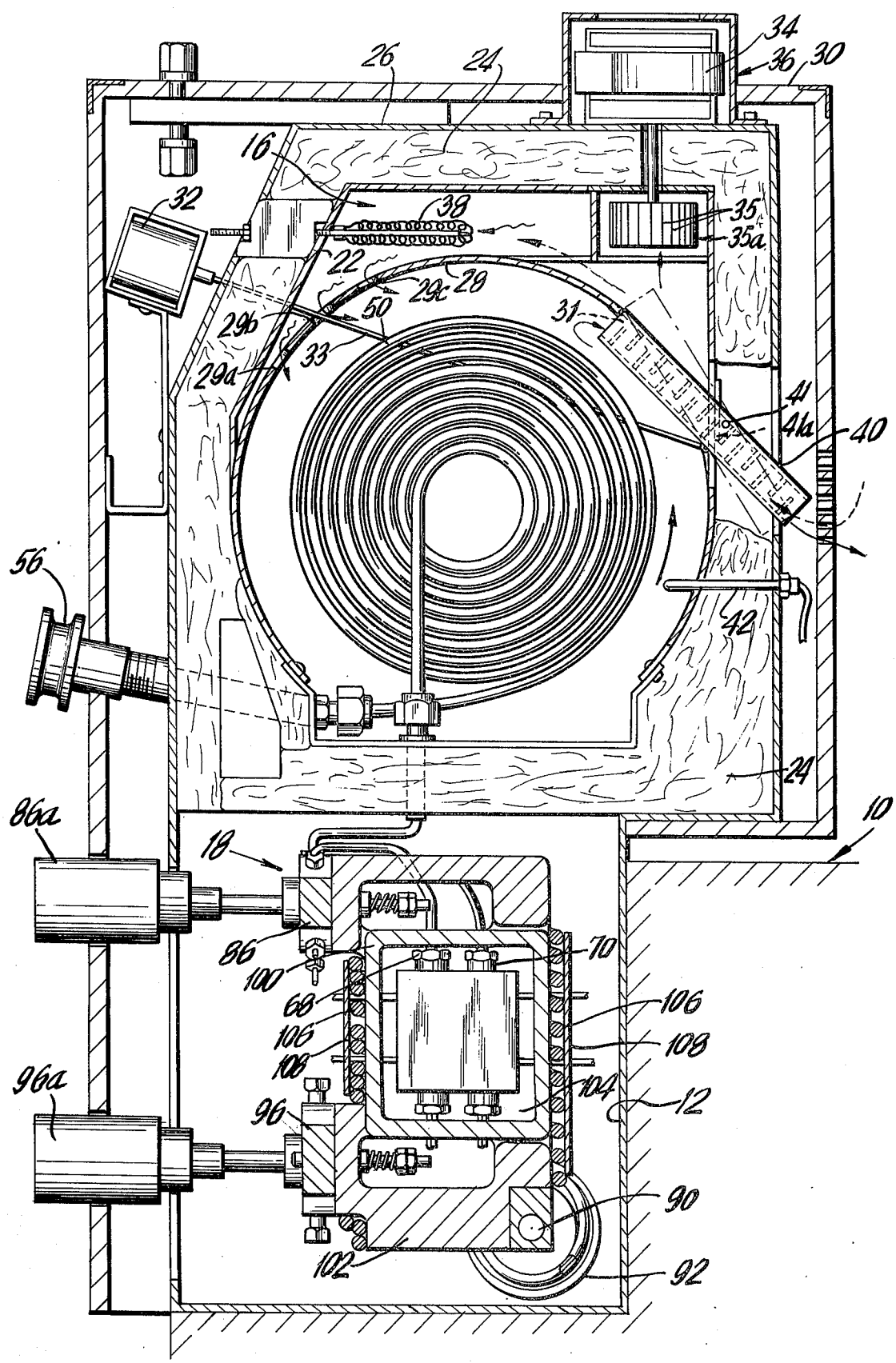
FIG. 2 is a cross section plan view taken on the plane 2—2 of the embodiment of my invention shown in FIG. 1.

Our improved gas chromatograph comprises an upper chamber 16 cojointed to a specifically dimensioned lower chamber 18. The lower chamber is of such dimension that it readily fits into the infrared spectrometer sample test well 12. The instrument industry has set standards for dimensions of fittings and accessories which are now widely adapted. Accordingly, our chromatograph may be readily combined with spectrum analysis equipment produced by most manufacturers. FIG. 2 shows the embodiment of the present invention, illustrated in FIG. 1 as seen in a cross section on plane 2—2. The relationship of the lower chamber 18 and the spectrometer test sample well 12 is readily visualized in FIG. 2. The upper chamber 16 is comprised of an inner liner 22, thermally insulated with packing insulation 24 between an outer panel 26 and the inner liner 22. The upper chamber 16 is mounted within a panelled frame 30 to provide rigidity to the whole assembly and to provide a base for mounting various other component parts of the chromatograph which will be described below.

The upper chamber 16 is provided with a curved baffle 28, mounted within but separated from the inner liner 22 in the upper portion of the chamber 16. The baffle 28 is provided with a number of small openings, 29a, 29b, 29c, for the flow of heated air into the interior region of the chamber 16 from the space between the baffle 28 and the inner liner 22. The means for heating the air in the space between the baffle 28 and the inner liner 22 will be described below.

Another opening, square in shape, in the baffle is provided at 31. A hinged rectangular air duct 40 provides both cool air intake and hot air exhaust flow from the interior of the chamber, depending upon the position of the hinged duct. The hinge 41 is mounted in a bracket 41a attached to the exterior of the inner liner 22. In FIG. 22, the solid line for the duct 40 shows it positioned to exhaust hot air from the interior of the chamber 16; the broken line illustration of the duct 40 shows it positioned to draw cool air into the space between the baffle 28 and the inner liner 22. In this latter position, the hinged rectangular duct 40 closes the square opening 31 in the baffle. Thus, the cool air is shunted above the baffle 31 where it is heated.

The hinged duct 40 is held in the desired position by the action of a solenoid 32 which actuates an extension arm 33. The extension arm 33 is attached to the hinged duct a distance below the hinged pivotal axis. Small movement of the solenoid armature and its extension arm will drive and hold the hinged duct to the respective cooling or heating cycle position depending upon the direction of the armature movement.

A thermostat 42 is mounted in the outer panel extending to the interior of the chamber 16. A small motor 34 is mounted external of the chamber 16, the shaft of which extends within the chamber and rotates a squirrel cage fan 35. The fan 35 is mounted within a fan housing 35a, positioned between the baffle 28 and the inner liner 22. A heating element 38 is mounted in the outflow portion of the fan housing. The thermostat 42 with its control means, not shown in the drawings, may be preset to actuate the solenoid 32, fan motor 34 and the heating element 38 to maintain the interior of the chamber at any prescribed temperature. Both heating and cooling cycles are provided within the automated temperature control system. Thus, the chamber 16 is a finely controlled temperature hot air oven for maintaining the chromatograph columns at the desired temperatures for optimal operation of the chromatograph.

The chromatograph is provided with two identical packed chromatograph columns, the first or analytic column 50, and the second or reference column 52 each, respectively, being coiled into a flat spiral. The spirals are positioned coaxially adjacent to one another within the interior of the upper chamber 16. Circulated thermostatically controlled warm air within the chamber maintains both columns at the pre-specified temperature throughout the respective lengths of the spirals. The spiraled juxtaposed positioning of the columns within the oven chamber 16 allows for equal and constant heating with less radiated heat loss into the environment about the chromatograph.

An injection port 56 is mounted to extend partially through the panelled frame 30 and partially into the chamber 16. The injection port is connected to the input of the analytic column 50. The injection port is separately thermostated, insulated and heated by means of a conductive heating coil 58.

Figure 3:
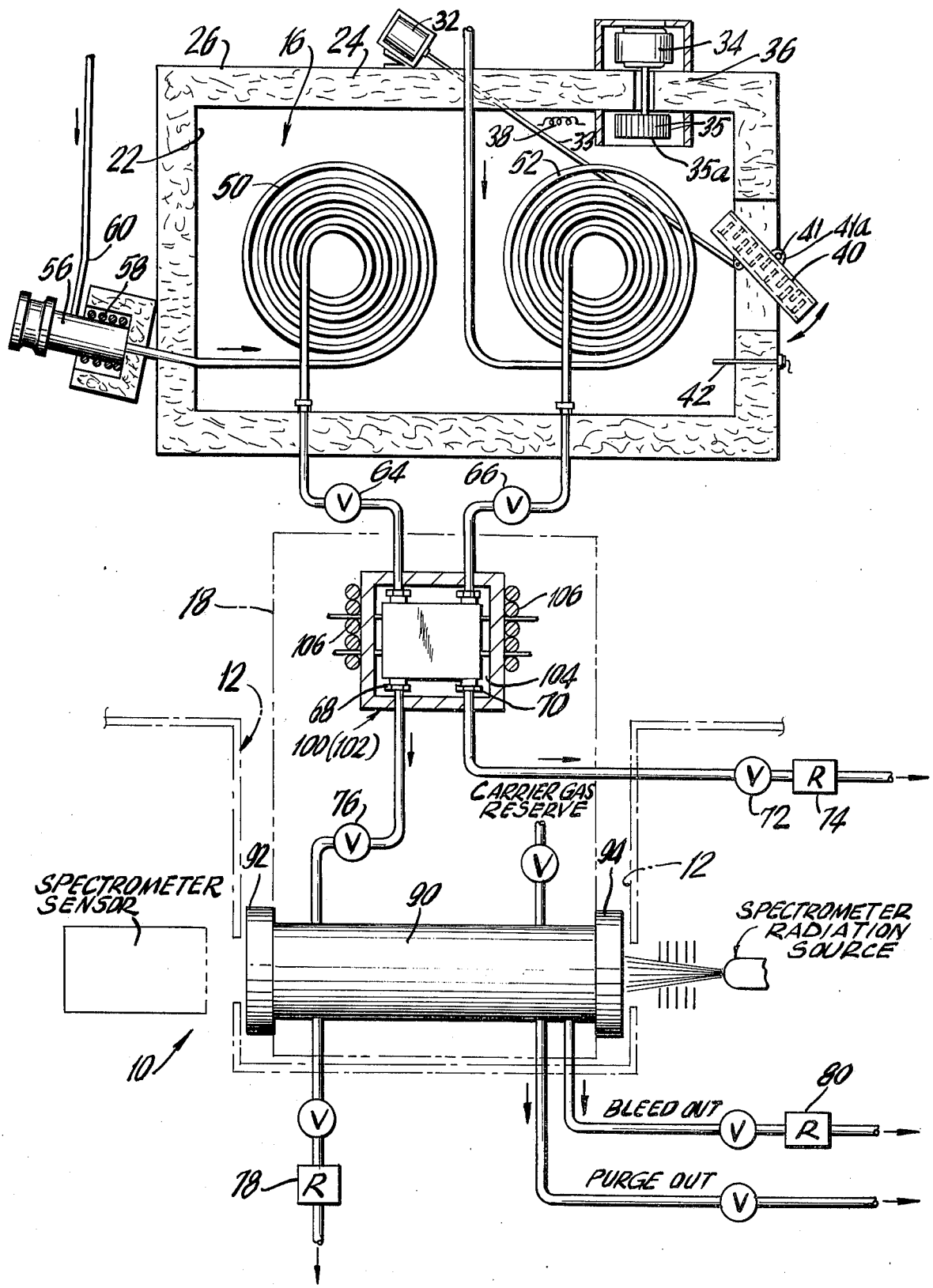
FIG. 3 is a schematic flow diagram of the embodiment of my invention shown in FIGS. 1 and 2.

FIG. 3 is a schematic drawing representative of the embodiment of our invention illustrated in FIGS. 1 and 2. The connections between the various components of the chromatograph may be readily seen in FIG. 3.

A carrier gas reserve, normally a pressurized tank (not illustrated), of helium, nitrogen or other suitable carrier gas is connected to the carrier gas inlet 60 of the injection port 56, and also to the input of the reference column 52. It is common practice to heat the carrier gas by some convenient means prior to its flowing into the reference column. While the direct connection between the carrier gas reserve and the reference column 52 as shown in the schematic FIG. 3 does not show preheating, such preheating procedure is conventional and often necessary for the proper functioning of the instrument.

The effluent gases emitted from the coiled columns 50 and 52, respectively, flow through valve means 64, 66 and into thermal conductivity detectors 68 and 70. From the reference detector 70, the gases flow through a stop valve 72 and a restrictor 74. From the analytic detector 68, the gases flow through a stop valve 76 and into a test sample cell 90 described below. The valves 64, 66 72 and 76, associated with the column effluents are referred to as column valves; and other valves described below associated with the test sample cell are referred to as sample cell valves. The column valves and the sample cell valves are combined, respectively, and form multiport column valve 86 and cell valve 96. The mounted positioning of the multiport valves 86 and 96 may be visualized by reference to FIGS. 1 and 2.

The test sample cell 90 is mounted transversely of the chamber 18. The test sample well 12 of the infrared spectrometer 10 permits insertion of a test sample cell within a beam of infrared radiation generated within the spectrometer. The test cell 90 is a hollow metal or glass chamber, windowed 92, 94, at either end. The windows are sealed to the chamber and are made of material reasonably transparent at the wavelengths of radiation to be used in the analysis. In infrared analysis, crystalline sodium chloride or sodium bromide are common window materials.

When the lower chamber 18 is set within the infrared spectrometer sample test well, the transversely mounted sample cell 90 is coaxial with and intercepts the spectrometer's infrared beam. This arrangement may be readily visualized by reference to the illustrations.

Extraneous heat, radiated or conductively transported into the spectrometer will interfere with the infrared absorption spectrum analysis. Accordingly, the insertion of the lower chamber 18 into the spectrometer sample test well requires care that excessive heat generated by the chromatograph operation does not interfere with the spectrometer operation. On the other hand, the eluted sample vapors issuing from the analytic column 50 must be maintained at a sufficiently high temperature to maintain a vapor state and prevent condensation on the cell windows and within the connecting tubes. The chromatograph thermo conductivity detectors 68 and 70 are adversely responsive to ambient temperature changes. To meet these diverse conditions, we have provided a novel mounting with thermal control of the component parts mounted thereto. Two heavily walled plates or castings 100, 102 contoured to provide, when juxtaposed, a recess 104 within which the two detectors 68 and 70 are mounted. Surfaces are provided on the plates 100, 102 for mounting in thermal contact the multiport column valve 86 and the multiport cell valve 96. Valve stems 86a and 96a, respectively, extend beyond the panelled frame 30 for convenient control of the valves. The sample cell 90 is also mounted to the plates 100 and 102 in controlled thermal contact. The plates 100, 102 comprise a sizable heat sink which is warmed by means of a heater coil 106. Radiant heat emitted from the heated plates 100, 102 is insulated from the adjacent spectrometer components by means of heat shielding 108. All tubular connections fro the columns, the detectors, sample cell and to atmospheric exhaust pass through the respective valves 86 and 96 as described above. The desired temperature of the gases issuing from the columns may be maintained and yet by means of the thermostated shielded heat sink plates 100 and 102, no excess extraneous heat is communicated to the spectrometer.

Our improved chromatograph in combination with absorption spectrum analyzers may firstly be utilized in conventional chromatographic procedures. Secondly, used on the "fly" for rapid partial analysis. And finally and thirdly, used in a stop flow mode with high pressure procedures. In the latter pressurized chromatograph method, the restrictors 74, 78 and 80 may be utilized in accordance with the methods and apparatus described in the inventions of HIRSCHFELD and MC NAIR, Ser. No. 553,990, filed Feb. 28, 1975 and HIRSCHFELD and BROWN, Ser. No. 553,989, filed Feb. 25, 1975 and other related applications. In conventional chromatographic procedures and "fly" analysis, the flow restrictors 74, 78 and 80 would normally be removed or preset at the open position.

The foregoing description and drawings are intended as merely illustrative of our invention, the scope of which is set forth in the following claims.

We claim:

1. An improved gas chromatograph in combination with an absorption spectrum analyzer, the chromatograph comprising upper and lower cojoined chambers, the lower chamber having measured dimensions, the absorption spectrum analyzer having a measured dimension test sample well, the chromatograph lower chamber being dimensioned to fit within the test sample well; the upper chamber being thermally insulated, provided with heating and thermostat means, the chromatograph further comprising a chromatograph column and an injection port, the column being mounted within the upper chamber and connected at its input to the injection port; a detector, a sample cell and a plurality of valves, the detector cell and at least two multiport valves being mounted juxtaposed to a heated thermostated metal plate means positioned within the lower chamber; the cell, when mounted to the aforesaid plate being positioned transversally of the lower chamber, short tubular connections between, respectively, the column and valves between the detector and valves, and between the cell and valves, whereby, eluted sample materials emitted by the column may be entrained and momentarily retained within the sample cell, the chromatograph lower chamber with the transverse sample cell being positioned within, yet thermally insulated from the analyzer test sample well, while absorption spectrum analysis procedures are completed.

2. The apparatus combination of claim 1 above wherein the absorption spectrum analyzer is an infrared spectrometer.

3. The apparatus combination of claim 1 above, a flow restrictor, wherein at least one valve port connects to the flow restrictor and the restrictor connects to exhaust into the atmosphere, whereby the chromatograph column pressure measured at the output of the column and the sample cell pressure may be maintained during operation at gauge pressures greater than one atmosphere.

4. The combination apparatus of claim 1, wherein the upper chamber heating means is comprised of means for heating and circulation of heated air through the chamber.

5. The combination device of claim 4, wherein the chromatograph column is wound into a flat spiral and mounted within the thermally insulated upper chamber with the axis of the flat spiral at right angles to the vertical.

6. The combination apparatus of claim 5 above, wherein there is a second chromatograph column, the second column being wound into a flat spiral and mounted juxtaposed and coaxially with the first column within the upper chamber whereby the first column is an analytic column and the second column is a reference column and both columns are maintained in identical thermal condition with the heated air circulating about them.

7. The combination apparatus of claim 1 above, wherein the heated thermostated plate means positioned within the lower chamber is comprised of a first and a second matching plates, the plates being recessed respectively to accommodate enclosed mounting of two thermal conductivity detectors within the juxtaposed plates, external surfaces upon the plates for mounting the two multiport valves, and an external concavity for mounting the sample cell, the valves and cell when mounted to the plates being in thermal contact therewith, and heater coils and thermostat means juxtaposed to the plates to maintain the plates assembled with the detectors, valves and sample cell within a specified temperature range, whereby the chromatograph components mounted within the lower chamber and adjacent to the absorption spectrum analyzer are maintained within a specified operating temperature, but the adjacent analyzer is not excessively heated by the chromatograph.

8. An improved gas chromatograph comprising an upper chamber and a lower chamber, the chambers being cojoined metal enclosures thermally insulated respectively one from the other, the chromatograph further comprising a chromatograph column and an injection port, the column being mounted within the upper chamber and connected at its input to the injection port heat generating means mounted within the upper chamber, adapted to maintain the column at an elevated temperature; a detector, a sample cell and a plurality of multiport valves, the detector cell and at least two multiport valves being mounted juxtaposed to a heated, insulated and thermostated metal plate means, the metal plate means being positioned within the lower chamber; the cell, when mounted to the aforesaid plate being positioned transversally of the lower chamber, short tubular connections between respectively, the column and valves, between the detector and valves, and between the cell and valves, whereby eluted sample materials emitted by the column may be entrained and momentarily retained within the sample cell, the chromatograph lower chamber enclosure with the transverse sample cell mounted therein thermally insulated from the upper chamber heat source, whereby absorption spectrum analysis procedures may be performed upon sample materials entrained within the cell without communicating excessive heat from the chromatograph through the lower chamber enclosure into juxtaposed absorption spectrum analysis equipment.

* * * * *